United States Patent [19]
Everhart

[11] Patent Number: 5,186,057
[45] Date of Patent: Feb. 16, 1993

[54] MULTI-BEAM LIQUID-DROP SIZE/RATE DETECTOR APPARATUS

[76] Inventor: Howard R. Everhart, 3808 Mt. Ainsworth Ave., San Diego, Calif. 92111

[21] Appl. No.: 779,865

[22] Filed: Oct. 21, 1991

[51] Int. Cl.⁵ .................. G01F 13/00; A61M 5/168
[52] U.S. Cl. ................... 73/861.41; 250/575; 356/379; 356/385; 604/253
[58] Field of Search ............ 73/861.41; 128/DIG. 13; 250/575, 577; 356/335, 379, 383, 385; 604/253

[56] References Cited

U.S. PATENT DOCUMENTS

| | | | |
|---|---|---|---|
| 2,880,764 | 4/1959 | Pelavin | 141/130 |
| 3,157,727 | 10/1964 | Nathan | 250/225 X |
| 3,500,366 | 3/1970 | Chesney | 340/222 |
| 3,563,090 | 2/1971 | Deltour | 73/861.41 |
| 3,591,290 | 7/1971 | Zinner et al. | 356/335 |
| 3,596,515 | 8/1971 | Cramer | 73/194 R |
| 4,314,484 | 2/1982 | Bowman | 73/861.41 |
| 4,397,648 | 8/1983 | Knute | 604/253 |
| 4,432,761 | 2/1984 | Dawe | 604/253 |
| 4,498,901 | 2/1985 | Finch | 604/65 |
| 4,509,943 | 4/1985 | Hanzawa | 604/31 |
| 4,529,309 | 7/1985 | Pettersson et al. | 356/335 |
| 4,680,977 | 7/1987 | Conero | 73/861.41 |
| 4,718,896 | 1/1988 | Arndt | 604/253 |
| 4,936,828 | 6/1990 | Chiang | 604/253 X |
| 5,074,658 | 12/1991 | Tavlarides et al. | 356/27 X |

Primary Examiner—Herbert Goldstein
Attorney, Agent, or Firm—Nydegger & Associates

[57] ABSTRACT

An apparatus for liquid flow detection especially adapted for use with an IV administration set includes an energy beam emitter device and an energy beam detector device. A drip chamber is connected in flow communication with a fluid reservoir of the IV administration set. Fluid flow is directed through a drop forming orifice into the drip chamber and thence into a supply tube for the IV administration set. The energy beam emitter device produces a pair of parallel spaced beams which are directed across the free fall path of the fluid drops and to the energy beam detector device. As the drops enter and exit the energy beams, signals are generated by the detector device as a function of time and are fed to a microprocessor. Using this data and relationships developed with conventional mathematics, the diameter of each drop can be extrapolated. From the drop diameter, the drop volume can then be calculated and used with the time measurements to provide extrapolated outputs of flow-rate and total volume. This data may be used for display or control purposes.

20 Claims, 1 Drawing Sheet

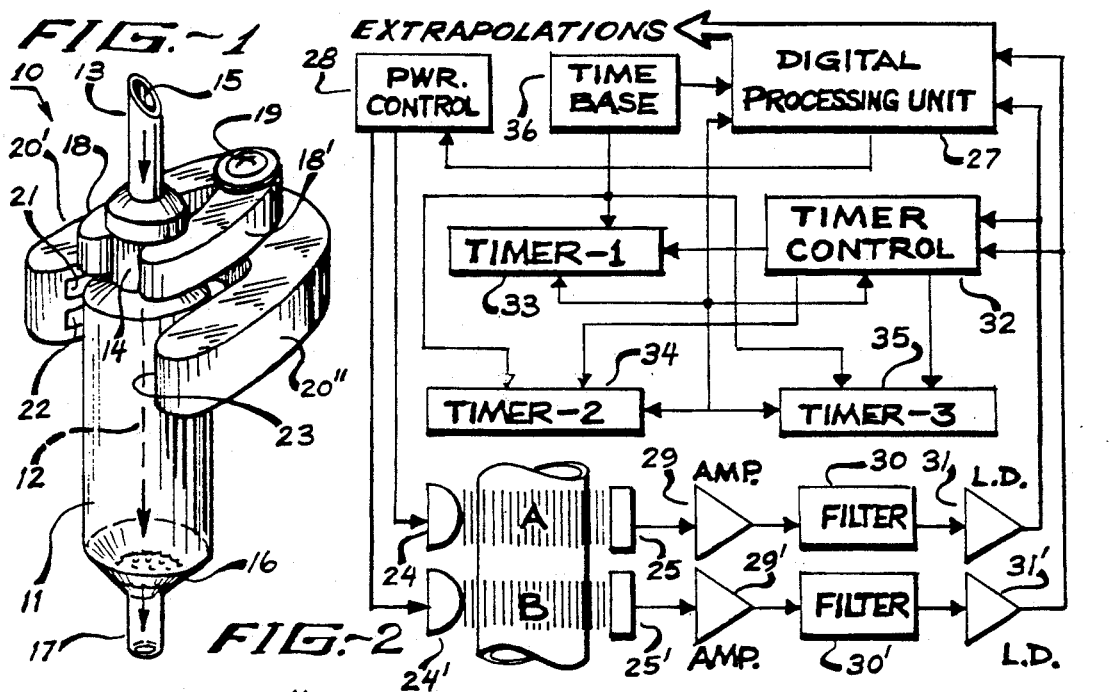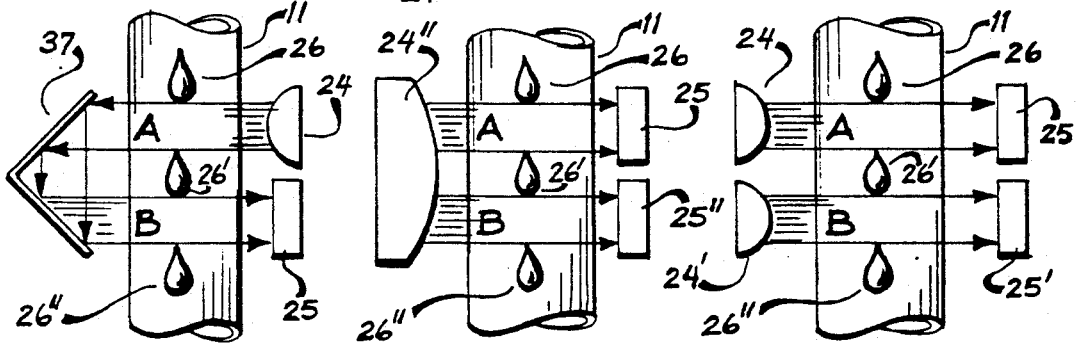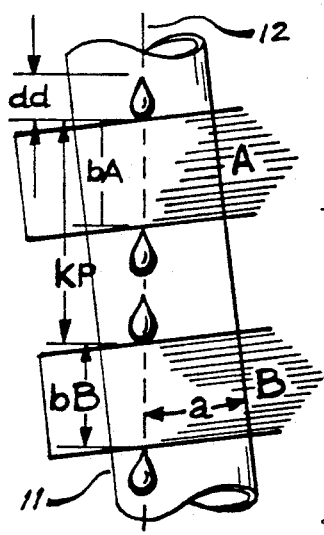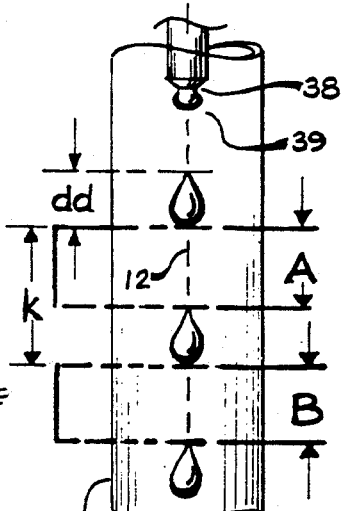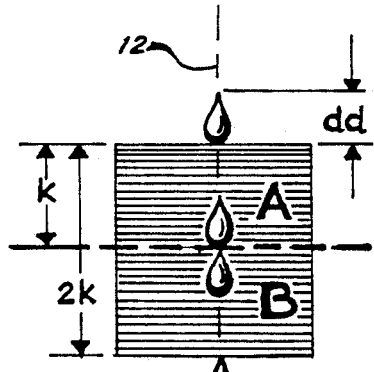

MULTI-BEAM LIQUID-DROP SIZE/RATE DETECTOR APPARATUS

BACKGROUND OF THE INVENTION

This invention relates to medical intravenous fluid-infusion apparatus, and more particularly it addresses fluid-flow type sensors thereof; for the purpose of detecting the quality and quantity of individual liquid-drop flow generally through a gravity drip-chamber assembly which may have other commercial application other than medical related.

Heretofore, there have been numerous related patent improvements in the above identified patent art field. For example, relevant early U.S. Pat. No. 2,880,764(filed May, 1957 by Pelavin for Technicon) features two vertically spaced apart devices, the upper being a photo-multiplier tube used as a triggering-device, the lower being a conventional cathode-ray video-tube utilizing a horizontal-sweep to measure droplet-width at a predetermined drop-point, the output voltage-amplitude of the camera being proportional to the diameter of the droplet; the system utilizes fixed timing-delay circuits which dictate fixed physical distances between the drop-forming orifice and the two beams, in other words requiring pre-calibrated delay-timers for each precise physical installation setup. This is a major problem when large variation in drop-size are present, due to the fact that large drops actually break away from the uppermost drop-forming orifice at a lower position, and therefore the exact drop-flight time between the upper and lower detectors is not always predictably fixed. Thus, nor is this invention readily adaptable to comparatively portable installation situations and does not tolerate significant variations in inadvertent drop-path tilt-angle, owing the change in optical image-size falling upon the camera-lens. Also, U.S. Pat. No. 3,500,366 (filed October, 1966 by Chesney for Gen.Instrument) features a single capacitive detector having dual-electrodes, which serves to detect the presence of a fluid droplet through disturbance of the electrical-field within the drip-chamber; a system which essentially serves to merely count drops, but maybe unfortunately readily upset as to reliability by proximity of ambient inductive objects or electromagnetic-fields, nor can the device read drop size.

Next, U.S. Pat. Nos. 3,563,090(filed September, 1968 by Deltour), and, 3,596,515(filed November, 1967 by Cramer for Ivac Co.) set forth fluid-flow sensor art capable of detecting and counting drops of liquid falling through a drip-chamber assembly. However, it has been found in the intervening years of usage in the field, that the so called "single blip"(electrical impulse) signal emanating from such apparatus is insufficient to provide truly adequate quality performance, in that only the number of drops is detected; yet importantly, the volume of the drops is not measured.

Later examples of liquid-drop flow-quality detector devices were found in U.S. Pat. No. 4,314,484 (filed October, 1979 by Bowman for Utah University), who demonstrate a single-blip sensor device in conjuction with ability to read variation in the quality of light-radiating from a source such as a L.E.D.(light-emitting diode); and U.S. Pat. No. 4,498,901(filed July, 1982 by Finch for Abbott Labs.) who also redemonstrates dynamic detection of droplets in the presence of changing light amplitude; and U.S. Pat. Nos. 4,397,648(filed November, 1980 by Knute for Ivac Co.), 4,509,943(filed August, 1982 by Hanzawa for T.K.Kaisha/Japan), 4,680,977(filed March, 1985 by Conero for Ivac Co.), all of which substantially mimic the notion of a single-blip liquid-drop drip-chamber flow-quanity detector means. Knute's improvement on the earlier Cramer disclosure was essentially that of an improved method of attachment to the drip-chamber, which enabled the producer-(Ivac Corp.) to foster a dedicated disposable(I.V.-set) for marketing posture.

Further relevant examples of more elaborate intravenous fluid-flow delivery systems utilizing liquid-drop flow measurement apparatus, are disclosed in U.S. Pat. No. 4,718,896 (filed January, 1986 by Arndt for Abbott Labs.) who shows a plurality of radiators and oppositely cooperating photodetectors, so as to thereby better detect drops even to a 30-degree cantering of the drop-chamber. Additionally, Arndt's invention facilitated a preliminary stage photocell-detector method by which to automatically detect the presence of an alternate drop-size reducing orifice-insert(chanulas). Both the Arndt's and Conero's inventions were outgrowths of standards adopted by AAMI(Assoc.for the Advancement of Medical Instrumentation), which delt with drop-chamber angularity.

Finally, U.S. Pat. No. 4,432,761(filed September, 1982 by Dawe for Abbott Labs.) introduced the notion of a gravity-tube constriction to obtain drop-column formation, ostensibly as a predictable flow rate detector, yet the method does not readily accomodate different viscosities of fluid, and requires a specialized drip-chamber having a gravity-tube of high dimensional accuracy.

Thus, although the fluid-flow sensors discussed above have other commercial applications in their ability to detect the flow of individual droplets of a fluid, a primary use of such sensors has been the detection of fluid-flow through a drip-chamber portion of an intrevenous fluid-infusion system.

GENERAL INFORMATION

An intravenous fluid-infusion system is comprised of a fluid filled upwardly suspended flexile-bag or bottle as the fluid reservoir, a small-diameter plastic-tubing by which fluid flows to the patient, and an intravenous catheter through which the fluid is directly administered into the patient's vein. The fluid-reservoir is positioned over the venipuncture-spike so that the gravitational force on the fluid causes the fluid to flow reliably therethrough to the patient. The intravenous(I.V.) fluid-administration setup consists of a drip-chamber assembly and a length of flexible-tubing with an associated fluid-flow regulating-clamp(or valve). The drip-chamber has a hollow spike on the top that is inserted into the fluid-reservoir, the fluid then flowing through the spike into a transparent cylindrical-chamber(sight-chamber) via a drop forming orifice where drops form and free-fall down through the chamber-cylinder. The bottom of the chamber is connected to the flexible-tubing and is partially filled with fluid to prevent the air in the chamber from also flowing into the catheter-line(-tubing). The drop forming orifice is designed to form a fixed number of drops for each milliliter of fluid flowing through the sight-chamber, and thus the flow rate can be visually-set by adjusting the regulating-clamp or valve located on the catheter feed-line, whereby the operator may visually count the number of droplets falling in a fixed time segment. Manual control requires the operator constantly check on the flow-rate, and owing to the depleting reservoir pressure, and cold-flow variation in the tubing(if a squeeze-clamp is used), etc. Therefore, the convenience of being able to accurately and reliably set the flow-rate is paramount in modern facilities, witness the considerable patent activity in this area, particularly now evolving around more sophisticated electronics.

The vital accuracy of these known state-of-the-art fluid delivery systems is actually limited by inability of the drop forming orifice to generate droplets of consistent volume, which is not only effected by the geometric shape of the orifice and associated components, but by the material from which it is constructed, the rate of fluid-flow, and the fluidic properties of the delivery such as viscosity and surface-tension characteristic; plus, the length of time in which the orifice has been exposed to the fluid deliver; Hence, inventors of this equipment have dealt with most of these factors, by closely controlling the geometry and materials employed; and by providing drop-volume vs. fluid-flow rate, and drop-volume vs. fluid-type compensation via use of computer-algorithms embed in the fluid-flow controller section of the delivery system. Implementation of these strategies necessarily depends heavily upon accurate user input of fluid-composition and maintance of the droplet forming orifice properties throughout the life-cycle of the manufactured product. Moreover, the control-section of the delivery system and the drip-chamber assembly, containing the droplet forming orifice, are cratically matched by the system strategy logic, and therefore adaptive mixing of system components among different manufactured brands, is not as a practical matter, regarded as safely interchangeable.

SUMMARY OF THE INVENTION

A. In view of the foregoing discussion about the earlier invention art, it is therefore important to make it clear to others interested in the art that the object of this invention is to provide a more consistantly accurate method by which to detect and extrapolate the actual volumetrics of a given droplet. This invention virtually eliminates the heretofore problematical issue of quantitative variation in drop-volume, by measuring the size of the drops falling through a given substantially conventional drip-chamber assembly; from which the volume of the droplet is then calculated. Therefore, a primary object of this invention is to provide a sensory-system utilizing two uniaxial so called Schlierens-systems, employing either refracting or reflecting beam-shaping elements(reflecting-elements being preferred owing to their general ease of installation and compactness of construction), the aggregate assemblage of which is quite readily interchangeable among different manufactured brands of drip-chamber apparatus(resulting in a economy advantage for the end user). Note also, that use of beam-shaping elements on the optical-emitter side is optional as multipul emitter sources may actually be employed to obtain a suitable optical energy beam.

B. Another object of this invention is to set forth a substantially conventional radiant energy emission generator device such as an L.E.D.(light-emitting diode) or I.R.(infrared-lamp) arranged abaxially(that is, immediately adjacent) to the fluid drop/flight-path axis, while projecting the radiant energy across the path upon an opposite first reflective surface where the beam is abaxially advanced beside the drop-path to a second reflective surface, whereby the beam becomes reflected back across the more advanced stage of the drop-path sector to a suitable substantially conventional radiant energy detector device; the signal blips derived therefrom being handled by a substantially conventional micro-processor appropriately programed to provide timing comparison of the signals, and thereby extrapolate relative volumetric data on the drop progressions, this monitoring apperatus thus serving to facilitate precise regulation of the drop flow rate.

C. Another object of this invention is to set forth a substantially conventional radiant energy device such as an LED or IR device arranged abaxially to the fluid drop/flight-path axis of an existing drip-chamber, the radiating device discretely projecting energy across the drop-path upon a first and a second radiant energy detector device, the second detector being staged more progressionally advanced adjacent to the drop-path axis; the signal blips derived therefrom being handled by a substantially conventional micro-processor appropriately programed to provide timing comparison of the signals, and thereby extrapolate relative volumetric data on the drop progressions, this monitoring apperatus thus serving to facilitate precise regulation of the drop flow rate.

D. Another object of this invention is to set forth substantially conventional first and second radiant energy generators such as LED or IR devices arranged successively and abaxially to an existing fluid drop-flight-path axis, while projecting the radiant energy across the path upon two opposite discrete conventional first and second energy detectors arranged abaxially opposite thereto; the signal blips derived therefrom being handled by a substantially conventional micro-processor appropriately programed to provide timing comparison of the signals, and thereby extrapolate relative volumetric data on the drop progressions, this monitoring apperatus thus serving to facilitate precise regulation of the drop flow rate.

DESCRIPTION OF THE PREFERRED EMBODIMENT DRAWINGS

The foregoing and still other objects of this invention will become fully apparent, along with various advantages and features of novelty residing in the persent embodiments, from study of the following description of the variant generic species embodiments and study of the ensuing description of these embodiments. Wherein indicia of reference are shown to match related points given in the test, as well as the claims section annexed hereto; and accordingly, a better understanding of the invention and the variant uses is intended, by reference to the drawings, which are considered as primarily exemplary and not to be therefore construed as restrictive in nature.

FIG. 1 is an exemplified side-elevation view of an existing drip-chamber, showing exemplified installation of the generic invention;

FIG. 2 is a diagrammatic representation revealing the preferred embodiment components of the generic invention in relation to an existing exemplified drip-chamber;

FIG. 3 is a diagrammatic side/elevation-view representation showing the basic preferred component arrangement of the generic invention;

FIG. 4 is a like diagrammatic side/elevation-view representation showing the basic preferred component arrangement of an alternate generic variant thereof;

FIG. 5 is a like diagrammatic side/elevation-view representation showing the basic preferred component arrangement of an alternate generic variant threof.

FIG. 6 is a side/elevation-view thereof, which however is shown as in an inadvertantly canted condition, exemplifying how the beam radiations of the invention still maintain discrete projection integrity relative to the drip-axis;

FIG. 7 is a side/elevation-view showing an exemplified drip-chamber and drop-former relationships;

FIG. 8 is a side/elevation-view showing the physical relationship of two projected beams having no noticable interjacent-gap.

ITEMIZED NOMENCLATURE REFERENCES 10- the assembled invention
11- drip-chamber
12- free-fall axis trejectory
13- venipuncture-spike
14- drip-forming section
15- drip flow-passage
16- drip collector region
17- lower outlet-pipe
18/18'- bifurcated finger clamps
19- mounting screw
20'/20''- DSU(detection-sensor unit) arms
21- initiating detector(EBD/energy-beam detector)
22- terminating detector(EBD-energy-beam detector)
23- EBE/energy-beam detector
24/24'/24''- EBE/energy-beam emitters(two small, one large)
25/25'- EBD/energy-beam detectors
26/26'/26''- downward drip progressions
27- DPU(digital-processing unit)
28- Power-control circuit
29/29'- amplifiers
30/30'- filters
31/31'- level-detectors
32- timer-control-circuit
33- timer- #1
34- timer- #2
35- timer- #3
36- timebase-timer
37- corner-mirror
38- drop-forming orifice
39- menisus forming drop

DETAILED DESCRIPTION OF THE PREFERRED EMBODIMENTS

Initial reference is given by way of FIG. 1, wherein is exhibited an exemplified medical I.V./drip-chamber assembly 10 generally having a tubular shaped drip-chamber body 11 which is typically made of a rigid transparent material so that the attendant may readily view the drip free-fall axis trajectory 12. The drip-chamber usually includes a hollow venipuncturing spike 13 atop the drip forming section 14, which is designed to penetrate an I.V.-container(reservoir, such as a flexible plastic-bag), whereby fluid flows down via the flow-passage 15 into a drop-forming orifice outlet just above the drip-chamber sometimes referred to as the fluid separation region(here hidden from view here). The drop thus falls into a collector region 16 where it then simply flows through a length of tubing(not shown) which attaches to the lower outlet-pipe 17 and onward via gravity-flow to a remote I.V.-catheter entering a patient's vein. Once the flow rate is known, actual regulation of the fluid has been adjusted via means of a tubing pinch-clamp or screw type needle-valve for example. Accuracy of the to be disclosed fluid size and rate monitoring apparatus of this instant invention, serves to maintain a much safer level of prescribed I.V.-fluid into the patient(including detection of parametric-variations such as effects on the system like ongoing changes in fluid-level prevailing in the I.V.-bag(or bottle), thus obviating occurrence of dangerously excessive or deficient flow-rates. Ability, to uniquely analyze the volume(drop-size and rate) on a real-time basis, and interpolate the extrapolated data into a suitable electrical value for automatic regulation of the I.V.-flow.

Bearing in mind this just described conventional drip-chamber, we also see how the also exemplified drop-sensing unit preferably includes a convenient universal annular-clamp having opposed spring-loaded bifurcated fingers 18/18' (or often an equivalent fixed-anvil like portion and a spring-loaded anvil portion) capable of holding fast upon drip-chamber housings of different outside-diameters, here attached to the sensoring-housing by means of mounting-screw 19. The said DSU(Detection-sensor Unit)-housing includes laterally opposed right 20' and left 20'' arm portions(which may be made to achieve the above clamping action), here shown housing the "initiate" 21(upper) and "terminate" 22(lower) detectors which receive an energy-beam here continually projected from a common emitter device 23 housed within the hidden region of the opposite side arm. In actual implementation for example, the optical energy (preferably of a frequency not identifiable by eye) is directed toward the detector(s) through a substantially conventional optical-window consisting of generally retangular-section, which is coated on all inner-facing surfaces with a non-reflective substrate so as to substantially negate spurious non-parallel energy propagation; thus attenuating any off axis projected energy that could otherwise create false-imaging at the detector.

Study of FIG. 2 reveals a suitable manner of electrical components in diagramatic fashion, which employs a special logic, which is likewise appropriately adaptable to the three generic variant DSU specimens of FIGS. 3, 4, 5 diagrams. We will come back to discussing this important diagram, but first we should review the three different sensor arrangements. FIG. 3 shows a substantially conventional energy-beam emitter(EBE) device 24 such as an LED or more preferably an infra-red-emitting device(IED) which projects an upper energy-beam "A" across through the drip-chamber 11 and through the free-fall trajectory-path 12, onto a double-reflector having a 90-degree interfacing-angle thereby folding the beam back across via lower passage "B" to a suitable substantially conventional energy-beam dector(EBD) 25; thus, facilitating evaluation of an ensuing drop 26 until it has transgressed downward to stage 26''. With this special arrangement of components, an interjacent-gap at least the height of a large drop must be held at 26, in order to maintain the discretion of a distinct double-blip signal as the fluid drops from the upper projection to the lower projection of the same beam.

FIG. 4 shows a perhaps ultimately compact embodiment, wherein a large EBE-device 24'' capable of simultaneously projecting two energy-beams A and B across upon two separate EBD-devices 25 and 25'; thus likewise facilitating evaluation of an ensuing drop 26 until it has translocated to point 26'' below. An advantage of this arrangement(as well as the following one), is that of reducing the need for a substantial interjacent-gap between the co-operative energy-beams to practically nill. Hence, FIG. 5 shows the third suggested embodiment, wherein a doublet pair set of EBEs 24 and 24' beam individual energy across via paths A and B through the drip-path axis 12 so as to land upon the two discrete EBDs 25' and 25".

Reference to FIG. 6 reveals how regardless as to being cantered over to a considerable attitude, the integrity of the discrete energy-beams A and B remain able to properly discern translocation of the fluid-drop as it progresses along the drop-path flight axis 12. This is an important quality, since the I.V./administration-rig is generally a vertical post standing upon a mobile castered base, thus prone to inadvertant dispositions of the hanging I.V.-bag and connected drip-chamber. A drip-chamber may appear to be hanging vertically, while when viewed from a 90-degree different azimuth viewing angle, may be shown to actually be askew(see exemplified ref.arrow angle "a") from the vertical axis 12.

The exhibit of FIG. 7 is a diagram demonstrating the general effect of a transient fluid-drop 26 as it transgresses the first("A") and second("B") sectors of beam projection within the drip-chamber 11, here including an exemplified drop-forming orifice 38 at which point a menisus 39 is shown forming a drop.

Hence, FIG. 7 refers to measuring the time for a drop to traverse the upper-beam(A), the equation for the distance is: "$dd+bA=(v0*t1)+(0.5*t1^2)$" where dd is the drop-diameter, bA is the upper-beam height(top edge to bottom edge), v0 is the drop-velocity upon beam entry, t1 is the measured time for the drop to traverse the upper-beam, and g is the gravitational-acceleration constant. Measuring the time for the drop to traverse the distance from a point in the upper-beam to an equivalent point in the lower-beam(such as the respective beam entry points); the equation is thusly: "$k=(v0*t2)+(0.5*g*t2^2)$" where k is the distance between the beam entry point, v0 is as said before, t2 is the measured time for the drop to travel down from the upper-beam to the lower-beam, and g is as said before.

Similarly, the equation for the distance traversed by the drop when traveling through both beams in terms of the measured time is: "$dd+k+bB=(v0*t3)+(0.5*g*t3^2)$" where dd and k are as said before, bB is the lower beam-height, v0 and g are as said before, and t3 is the measured-time. Therefore, FIG. 7 illustrates the relationship of the distances used in the equations. Accordingly, it can be seen from the equations that each contains only two unknowns, v0 and dd, and thus the drop-diameter(dd) can be found from any pair of the three equations. The equations however, are only correct if the drop falls exactly perpendicular to the beam-axis. In practice, this is hardly ever the case, and as FIG. 6 illustrates, the dimensions are actually altered proportionally with the angle between the actual drop-path and the perpendicular of the beam's axis. This adds then a third unknown, and therefore the simultaneous solution to all three equations is required to reliably find the true drop-diameter(dd), as a function of fluid volume.

A physical arrangement of the components that is of further interest, would be that of FIG. 8 but wherein there would be "no" noticeable interjacent-gap between the two substantially parallel energy-beams. This arrangement would actually simplify the equations such that the actual beam widths and the actual beam-to-beam distance are preferably equal(as k). Thus, when there is an angle between the drop and drip-chamber axis, as in FIG. 6, the distances (k) are actually larger, and can be calculated from the measured times as: "$kp=(0.5*g*t2*(t3^2-t1^2+(t1*t2)-(t2*t3)))/(t1+t2-t3)$" wherein kp is the actual-distance, g is the acceleration due to gravity, t1 is the time required to pass down through the upper-beam, t2 is the time required to travel down from the upper-beam to the lower-beam, and t3 is the time required to pass down through both beams. The length of the drop(tip-to-tail, as it were) can then be extrapolated from: "$dd=((t1-t2)*(kp+(0.5*g*t1*t2)))/t2$" wherein dd is the drop-length (actually approximately the drop-diameter as observed via hi-speed photography) and the remaining notation is as defined for kp. Note, that the foregoing equations are considered exemplary, as other implementations may be employed.

Thus, as a practical matter, the drop-volume can be approximated from the drop-length using: "$volume=(4*pi*dr^3)/3$" wherein pi is the ratio of a circle's circumference to its diameter, and dr is equal to dd from the second to the last equation above, divided by two. Additional volume changes may be made based upon v0 to correct for non-spherical drop shapes.

Referring now back to FIG. 2, one may more readily understand the exemplified circuit diagram logic, wherein power to the EBEs 24 and 24' beamed across to the two discrete EBDs 25 and 25' is controlled by the DPU(digital-processing unit) 27 via the power-control circuit 28. This enables the EBEs 24 and 24' to be amplitude-modulated at a fixed frequency. The optical-energy now reaching the EBDs 25/25' is next increased via amplifiers 29/29' and filtered 30/30' before entering the level-detectors 31/31' respectively. The amplifiers 29/29' increase the gain of the EBDs 25/25' and reduces the load on them to optimize the response times. The filters 30/30' are substantially conventional band-pass filters at the EBE 24/24' modulation-frequency used to remove "noise" from any ambient optical energy sources such as fluorescent-lamps. The level-detectors 31/31' are used to convert the signal to digital levels. The output of the level-detectors is connected to both the DPU 27 and the timer-control circuit 32. The DPU 27 examines the states of the level-detectors 31/31' periodically to determine if a drop-event has occured. This prevents non-drop events, such as condensation forming on the drip-chamber wall, or droplets splashing inside the drip-chamber, from falsely initiating the timers. The logic of the timer-control circuit 32 enables the counting of the timers 33, 34, 35 at the very rate of the timebase-timer 36. Timer-1(33) starts counting when the level-detector 31(upper-beam) goes low, and stops when the level-detector returns high. Timer-2(34) starts counting when the level-detector 31(upper-beam) goes low, and stops when the level-detector 31'(lower-beam) goes low. Timer-3(35) starts when the level-detector 31 for the upper-beam goes low, and stops when the level-detector 31' for the lower-beam returns high. When the DPU 27 determines that the correct sequence of the level-detectors output has occurred for a fluid-drop event, it reads the counts from the timers 33, 34, 35, and then resets the counts to zero. When sequences other than those of a drop event occur, the DPU 27 resets the timer-control logic and the timer counts to zero. Non-drop events are tracked by the DPU 27 to detect possible malfunctions. Upon detection of a fluid-drop event, the timer counts are used by the DPU to calculate the drop-volume using the last three previously discussed equations. The drop-volume can then be combined with the time between drops, which is maintained in the DPU, to provide extrapolated outputs of flow-rate and total-volume for display or control purposes.

Accordingly, it is understood that the utility of the foregoing adaptations of this invention are not necessarily dependent upon any prevailing invention patent: and while the present invention has been well described hereinbefore by way of preferred embodiments, it is to be realized that various changes, alterations, rearrangements, and obvious modifications may be resorted to by those skilled in the art to which it relates, without substantially departing from the implied spirit and scope of the instant invention. Therefore, the invention has been disclosed herein by way of example, and not as imposed limitation.

What is claimed of proprietary inventive origin is:

1. A method for extrapolating the volume of a free falling fluid drop comprising:
   generating a first energy beam having a predetermined height (A) and a second energy beam having a predetermined height (B), to cross a path of the free falling fluid drop, with an upper edge of the first beam separated from an upper edge of the second beam by a predetermined distance (k);
   measuring a time (t1) for the drop to pass through the first beam;
   measuring a time (t2) for the drop to pass from a predetermined point within the first beam to a predetermined point within the second beam;
   measuring a time (t3) for the drop to pass through the first and second beams;
   calculating an approximate drop diameter (dd) using conventional mathematical relationships between the predetermined heights (A and B), the predetermined distance (k), the measured times (t1, t2 and t3) and a gravitational acceleration constant (g); and
   calculating a fluid volume of the drop based on the drop diameter.

2. The method as claimed in claim 1 and further comprising calculating a fluid flow rate using the calculated fluid volume and timed intervals.

3. The method as claimed in claim 1 and wherein calculating the drop diameter (dd) is by solving three equations based on mathematical relationships between the predetermined heights (A and B), the predetermined distance (k) the measured times (t1, t2 and t3) and the gravitational acceleration constant (g).

4. The method as claimed in claim 1 and wherein the calculating steps are performed with a microprocessor.

5. The method as claimed in claim 1 and further comprising displaying calculated data.

6. The method as claimed in claim 1 and further comprising controlling a fluid flow rate using the calculated data.

7. An apparatus for determining a fluid flow rate in a fluid drop forming system comprising:
   energy beam emission means for directing first and second energy beams across a path of a free falling fluid drop with each energy beam having a predetermined height and with an upper surface of the first energy beam separated from an upper surface of the second energy beam by a predetermined distance (k);
   energy beam detection means for receiving the first and second energy beams and for generating signals in response to the fluid drop entering or exiting from a path of the first or second energy beams;
   timing means for receiving signals from the energy beam detection means and for measuring a time interval (t1) for the fluid drop to traverse the first beam, a time interval (t2) for the fluid drop to travel from a point within the first beam to a point within the second beam and a time interval (t3) for the fluid drop to travel through the first and second beams; and
   microprocessing means for receiving signals from the energy beam detection means and the timing means and for calculating an approximate diameter (dd) of the fluid drop from mathematical relationship between the predetermined heights of the energy beams, the predetermined distance (k), the time intervals (t1, t2, t3) and a gravitational constant (g) and then for calculating a fluid drop volume and a fluid flow rate.

8. The apparatus as claimed in claim 7 and further comprising display means for displaying data from the microprocessing means.

9. The apparatus as claimed in claim 7 and further comprising control means for controlling the fluid flow rate responsive to the calculated fluid flow rate.

10. The apparatus as claimed in claim 7 and wherein the energy beam emission means comprises an LED device.

11. The apparatus as claimed in claim 7 and wherein the energy beam emission means an IR emission device.

12. The apparatus as claimed in claim 7 and wherein the energy beam emission means produces a single beam that is split into two separate beams.

13. The apparatus as claimed in claim 12 and wherein the energy beam is split into two separate beams by a reflecting means.

14. The apparatus as claimed in claim 7 and wherein the energy beam emission means includes two separate energy beam emission devices.

15. In an IV administration system having a fluid source fluidly connected to a drop forming orifice adapted to direct fluid drops from the fluid source in free fall through a drip chamber in fluid communication with an IV tube connected to a patient, a system for measuring fluid flow comprising:
   energy beam emission means for directing an upper beam of a predetermined height (A) and a lower beam of a predetermined height (B) across the path of fluid drops falling through the drip chamber with the beams having upper surfaces separated by a predetermined distance (k);
   energy beam detection means for receiving the first or second energy beams and for generating signals in response to the fluid drops entering and exiting the path of the energy beams;
   timing means for receiving signals from the energy beam detection means and for timing a time interval (t1) for a drop to pass through the first beam, a time interval (t2) for the drop to pass from an upper surface of the first beam to an upper surface of the second beam and a time interval (t3) for the drop to pass through the upper and lower beams; and
   processing means for receiving signals from the energy beam detection means and timing means and for calculating the fluid flow rate based on mathematical relationships between the predetermined heights (A and B), the predetermined distance (k), the time intervals (t1, t2, t3) and a gravitational constant (g).

16. The system as claimed in claim 15 and further comprising holding means for mounting the energy beam emission means and energy beam detection means to the drip chamber.

17. The system as claimed in claim 16 and wherein the holding means comprises a pair of arms adapted to adjustably attach to the drip chamber.

18. The system as claimed in claim 17 and wherein the energy beam emission means and detection means are mounted within a recess formed in the pair of arms.

19. The system as claimed in claim 18 and wherein a single beam produced by the energy beam emission means is split into two beams using a reflector.

20. The system as claimed in claim 17 and wherein the energy beam emission means comprises two separate beam emission devices.

* * * * *